United States Patent
Van Beek et al.

(10) Patent No.: US 7,671,973 B2
(45) Date of Patent: *Mar. 2, 2010

(54) OPTICAL ANALYSIS SYSTEM USING MULTIVARIATE OPTICAL ELEMENTS

(75) Inventors: Michael Cornelis Van Beek, Eindhoven (NL); Frank Jeroen Pieter Schuurmans, Valkenswaard (NL); Levinus Pieter Bakker, Helmond (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 791 days.

This patent is subject to a terminal disclaimer.

(21) Appl. No.: 10/596,564

(22) PCT Filed: Dec. 16, 2004

(86) PCT No.: PCT/IB2004/052832

§ 371 (c)(1),
(2), (4) Date: Jun. 16, 2006

(87) PCT Pub. No.: WO2005/062006

PCT Pub. Date: Jul. 7, 2005

(65) Prior Publication Data

US 2007/0177240 A1    Aug. 2, 2007

(30) Foreign Application Priority Data

Dec. 19, 2003 (WO) .................. PCT/IB03/06089
Jun. 16, 2004 (EP) ...................... 04102762

(51) Int. Cl.
   *G01N 33/48* (2006.01)
(52) U.S. Cl. ....................................... 356/39
(58) Field of Classification Search ............... 356/39
   See application file for complete search history.

(56) References Cited

U.S. PATENT DOCUMENTS

| | | | |
|---|---|---|---|
| 5,090,807 A | 2/1992 | Tai | |
| 5,748,308 A | 5/1998 | Lindberg et al. | |
| 6,198,531 B1* | 3/2001 | Myrick et al. | 356/300 |
| 2003/0205673 A1 | 11/2003 | Williams | |
| 2004/0147034 A1* | 7/2004 | Gore et al. | 436/95 |

(Continued)

FOREIGN PATENT DOCUMENTS

WO    WO 02/057759 A1    7/2002

OTHER PUBLICATIONS

Soyemi, O.O., et al.; Design of Angle-Tolerant Multivariate Optical Elements for Chemical Imaging; 2002; Applied Optics; 41(10)1936-1941.

*Primary Examiner*—Roy Punnoose

(57) ABSTRACT

The present invention provides an optical analysis system for determining an amplitude of a principal component of an optical signal. The principal component is indicative of the concentration of a particular compound or various compounds of a substance that is subject to spectroscopic analysis. The optical signal is subject to wavelength selective weighting and wavelength selective spatial separation specified by a weighting function. The optical signal is preferably separated into two parts that corresponding to a positive and negative spectral band of the weighting function, respectively. The separation provides separate detection of the separated parts of the optical signal without significant loss of intensity, thereby providing an improved signal to noise ratio of the determined principal component. Separation and weighting of the optical signal is realized by two multivariate optical elements.

17 Claims, 10 Drawing Sheets

U.S. PATENT DOCUMENTS

2004/0158592 A1* 8/2004 Nikitin et al. ............... 708/400
2008/0094623 A1* 4/2008 Schuurmans et al. ........ 356/306
2008/0309930 A1* 12/2008 Rensen ....................... 356/300

* cited by examiner

OPTICAL ANALYSIS SYSTEM USING MULTIVARIATE OPTICAL ELEMENTS

BACKGROUND

The present invention relates to the field of optical spectroscopy.

Spectroscopic techniques are widely used for determination of the composition of a substance. By spectrally analyzing an optical signal, i.e. a spectroscopic optical signal, the concentration of a particular compound of the substance can be precisely determined. The concentration of a particular substance is typically given by an amplitude of a principal component of an optical signal.

U.S. Pat. No. 6,198,531 B1 discloses an embodiment of an optical analysis system for determining an amplitude of a principal component of an optical signal. The known optical analysis system is part of a spectroscopic analysis system suited for, e.g., analyzing which compounds are comprised at which concentrations in a sample. It is well known that light interacting with the sample carries away information about the compounds and their concentrations. The underlying physical processes are exploited in optical spectroscopic techniques in which light of a light source such as, e.g., a laser, a lamp or light emitting diode is directed to the sample for generating an optical signal which carries this information.

For example, light may be absorbed by the sample. Alternatively or in addition, light of a known wavelength may interact with the sample and thereby generate light at a different wavelength due to, e.g., a Raman process. The transmitted and/or generated light then constitutes the optical signal which may also be referred to as the spectrum. The relative intensity of the optical signal as function of the wavelength is then indicative for the compounds comprised in the sample and their concentrations.

To identify the compounds comprised in the sample and to determine their concentrations the optical signal has to be analyzed. In the known optical analysis system the optical signal is analyzed by dedicated hardware comprising an optical filter. This optical filter has a transmission which depends on the wavelength, i.e. it is designed to weight the optical signal by a spectral weighting function which is given by the wavelength dependent transmission. The spectral weighting function is chosen such that the total intensity of the weighted optical signal, i.e. of the light transmitted by the filter, is directly proportional to the concentration of a particular compound. Such an optical filter is also denoted as multivariate optical element (MOE). This intensity can then be conveniently detected by a detector such as, e.g., a photo diode. For every compound a dedicated optical filter with a characteristic spectral weighting function is used. The optical filter may be, e.g., an interference filter having a transmission constituting the desired weighting function.

For a successful implementation of this analysis scheme it is essential to know the spectral weighting functions. They may be obtained, e.g., by performing a principal component analysis of a set comprising N spectra of N pure compounds of known concentration where N is an integer. Each spectrum comprises the intensity of the corresponding optical signal at M different wavelengths where M is an integer as well. Typically, M is much larger than N. Each spectrum containing M intensities at corresponding M wavelengths constitutes an M dimensional vector whose M components are these intensities. These vectors are subjected to a linear-algebraic process known as singular value decomposition (SVD) which is at the heart of principal component analysis and which is well understood in this art.

As a result of the SVD a set of N eigenvectors $z_n$ with n being a positive integer smaller than N+1 is obtained. The eigenvectors $z_n$ are linear combinations of the original N spectra and often referred to as principal components or principal component vectors. Typically, the principal components are mutually orthogonal and determined as normalized vectors with $|z_n|=1$. Using the principal components $z_n$, the optical signal of a sample comprising the compounds of unknown concentration may be described by the combination of the normalized principal components multiplied by the appropriate scalar multipliers:

$$x_1z_1 + x_2z_2 + \ldots + x_nz_n,$$

The scalar multipliers $x_n$ with n being a positive integer smaller than N+1 may be considered the amplitudes of the principal components $z_n$ in a given optical signal. Each multiplier $x_n$ can be determined by treating the optical signal as a vector in the M dimensional wavelength space and calculating the direct product of this vector with a principal component vector $z_n$.

The result yields the amplitude $x_n$ of the optical signal in the direction of the normalized eigenvector $z_n$. The amplitudes $x_n$ correspond to the concentrations of the N compounds.

In the known optical analysis system the calculation of the direct product between the vector representing the optical signal and the eigenvector representing the principal component is implemented in the hardware of the optical analysis system by means of the optical filter. The optical filter has a transmittance such that it weights the optical signal according to the components of the eigenvector representing the principal component, i.e. the principal component vector constitutes the spectral weighting function. The filtered optical signal can be detected by a detector which generates a signal with an amplitude proportional to the amplitude of the principal component and thus to the concentration of the corresponding compound.

In a physical sense, each principal component is a constructed "spectrum" with a shape in a wavelength range within the optical signal. In contrast to a real spectrum, a principal component may comprise a positive part in a first spectral range and a negative part in a second spectral range. In this case the vector representing this principal component has positive components for the wavelengths corresponding to the first spectral range and negative components for the wavelengths corresponding to the second spectral range.

In an embodiment the known optical analysis system is designed to perform the calculation of the direct product between the vector representing the optical signal and the eigenvector representing the principal component in the hardware in cases where the principal component comprises a positive part and a negative part. To this end, a part of the optical signal is directed to a first filter which weights the optical signal by a first spectral weighting function corresponding to the positive part of the principal component, and a further part of the optical signal is directed to a second filter which weights the optical signal by a second spectral weighting function corresponding to the negative part of the principal component. The light transmitted by the first filter and by the second filter are detected by a first detector and a second detector, respectively. The signal of the second detector is then subtracted from the signal of the first detector, resulting in a signal with an amplitude corresponding to the concentration.

In another embodiment the known optical analysis system is able to determine the concentrations of a first compound and of a second compound by measuring the amplitudes of a corresponding first principal component and of a second principal component. To this end, a part of the optical signal is directed to a first filter which weights the optical signal by a first spectral weighting function corresponding to the first principal component, and a further part of the optical signal is directed a second filter which weights the optical signal by a second spectral weighting function corresponding to the second principal component. The light transmitted by the first filter and by the second filter are detected by a first detector and a second detector, respectively. The signal of the first detector and of the second detector correspond to the amplitudes of the first principal component and of the second principal component, respectively.

It is a disadvantage of the known optical analysis system that the signal to noise ratio is relatively low.

The present invention therefore aims to provide an optical analysis system of the kind described above, which is able to provide a signal with a relatively high signal to noise ratio.

The present invention provides an optical analysis system for determining an amplitude of a principal component of an optical signal. The optical analysis system comprises a first multivariate optical element, a second multivariate optical element, a first and a second detector. The first multivariate optical element is adapted for wavelength selective separation of the optical signal into a first part and a second part. The second multivariate optical element is adapted for wavelength selective weighting of the optical signal on the basis of a spectral weighting function. In particular, weighting of the optical signal refers to weighting of the first part and the second part of the optical signal. The first detector is adapted for detecting the weighted first part of the optical signal and the second detector is adapted for detecting the weighted second part of the optical signal respectively.

SUMMARY

The invention is based on the insight that the signal to noise ratio is relatively low in the known optical analysis system because a significant part of the optical signal is not detected by any of the detectors, but blocked by, e.g., the first optical filter or by the second optical filter. For instance, the optical signal received by the first optical filter comprises all information but the first filter transmits only that part of the optical signal corresponding to the first weighting function whereas the part of the optical signal corresponding to the second weighting function is blocked by the filter. The light blocked by the first optical filter and by the second optical filter is not detected which reduces the signal to noise ratio.

Preferably, the first part and the second part of the optical signal are spatially separated by means of the first multivariate optical element. The first part and the second part refer to different spectral ranges of the optical signal. Preferably, the first part of the optical signal refers to a positive part of the principal component and the second part of the optical signal refers to a negative part of the principal component. The first and second part are by no means restricted to a single spectral range Moreover each part of the optical signal may refer to various specific spectral ranges or spectral bands. For example, the first optical signal may refer to a combined spectral range of 850-870 nm and 900-920 nm. By selectively separating the first and second parts of the optical signal and by detecting the first and second parts by respective detectors the signal to noise ratio can be appreciably enhanced compared to prior art solutions.

In principle, no optical filters have to be applied at the detectors in order to filter an appropriate part of the optical signal. Additional to the wavelength selective separation of the optical signal into a first and second part, the second multivariate optical element applies a wavelength selective weighting of the optical signal on the basis of a spectral weighting function. Application of the wavelength selective weighting may apply to the optical signal before or after it becomes subject to a wavelength selective separation provided by the first multivariate optical element In this way, application of a wavelength selective weighting can be performed on the optical signal or on the first and second parts of the optical signal. Wavelength selective separation and weighting can be performed in an arbitrary order. Either the optical signal is first incident on the first MOE or on the second MOE, and thereafter it may be separately incident on the second and first MOE, respectively. The order in which the effect of first and the second MOE is applied to the optical signal may generally be arbitrary.

Weighting may occur before a separation takes place and vice versa. Also, the first and the second multivariate optical elements can be combined in such a way that the wavelength selective separation and the wavelength selective weighting of the optical signal is performed in a combined way. However, by spatially separating the optical signal into first and second parts and by selectively detecting the weighted first and second parts of the optical signal, the signal to noise ratio can be appreciably enhanced compared to prior art solutions making use of optical filters.

According to a further preferred embodiment of the invention, the optical analysis system further comprises a dispersive optical element to spectrally disperse the optical signal. The first and the second multivariate optical elements are arranged to ,receive the dispersed optical signal. The dispersive element can be realized by e.g. a grating or a prism for spectrally dispersing the optical signal. In this way the various spectral components of the optical signal can be spatially separated. By implementing the first and/or the second multivariate optical element as a spatial optical modulator, a wavelength selective modulation of the optical signal can be effectively realized. Modulations typically refer to modulation of the polarization and/or amplitude or intensity of the optical signal or, the first and/or second part of the optical signal.

The spectrally dispersed optical signal is received by the first and the second multivariate optical elements, i.e. different parts of the first and the second multivariate optical elements receive different wavelengths intervals or bands of the optical signal or parts of the optical signal. For individual wavelengths the first multivariate optical element is adapted to direct a first part of the optical signal to the first detector and to direct a second part of the optical signal to the second detector. Correspondingly, the second multivariate optical element, e.g. selective parts of the second multivariate optical element are adapted to individually weight different wavelengths components of the optical signal. Thus instead of partly blocking the optical signal as is done by the first optical filter and the second optical filter of the known optical analysis system, the different parts of the optical signal are directed to different detectors. As a consequence a larger amount of the optical signal is detected, yielding an improved signal to noise ratio.

According to the invention the optical signal is not restricted to optical signals having wavelengths which are visible by the human eye. The optical signal may comprise spectral components in the ultra violet (UV) and/or in the infra red (IR) spectral. Here, the IR spectral range may comprise the near infra red (NIR) and the far infra red (FIR) which has a frequency above 1 THz, and all intermediate wavelengths as well.

According to the invention the principal component is not limited to a pure principal component. Here, a pure principal component refers to a mathematically exact eigenvector for a certain compound. A principal component may also comprise minor contributions from other compounds which may result from imperfections during determining the principal components. A principal component may also correspond to a mixture of several compounds of known concentrations.

In an embodiment the principal component comprises a positive part in a first spectral range and a negative part in a second spectral range, the first part of the optical signal weighted by the first spectral weighting function corresponding to the positive part, the second part of the optical signal weighted by the second spectral weighting function corresponding to the negative part, the first detector and the second detector being coupled to a signal processor arranged to subtract a signal generated by the second detector from a signal generated by the first detector. In this embodiment an optical signal comprising a principal component having a positive part and a negative part can be analyzed with an improved signal to noise ratio. Typically, the first spectral range is free from the second spectral range.

According to a further preferred embodiment of the invention, the first multivariate optical element comprises a first region for receiving a spectral portion of the dispersed optical signal. This first region is adapted to modify the polarization of the dispersed optical signal. In this embodiment, the first multivariate optical element is implemented as a spatial optical modulator being adapted for spatial selective modulation of the polarization state of the dispersed optical signal. Hence the first region of the first multivariate optical element receives different wavelengths of the optical signal at different positions. The first region is furthermore adapted to modify the polarization of the dispersed optical signal in different ways at the different positions of the first region. In this way different wavelengths of the dispersed optical signal become subject to different polarization modifications. Depending on the granularity of the first multivariate optical element and the dispersion of the optical signal, hence the spectral range of the spectral portion that is received by the first region, particular spectral ranges of the received optical signal can become subject to a modification of polarization.

The dispersed optical signal therefore becomes subject to wavelength selective modification of polarization. In particular in combination with a polarization sensitive element like e.g. a polarizing beam splitter, a spatial separation of different spectral ranges can be effectively realized with a marginal loss of intensity. In this way first and second spectral ranges referring to positive and negative parts of the principal component can be effectively spatially separated for separate detection by respective. detectors.

According to a further preferred embodiment of the invention, the second multivariate optical element comprises a second region for receiving a spectral portion of the dispersed optical signal. The second region has a transmission or reflectivity that relates to the spectral weighting function. Preferably, the second multivariate optical element is implemented as a spatial modulator operating in reflection or transmission mode. Similarly as the first multivariate optical element also the second multivariate optical element may provide different transmission or reflection properties across the second region. In this way particular spectral ranges of the optical signal can become subject to amplitude and/or intensity modulation. In this way particular spectral components of the optical signal can effectively become subject to a wavelength selective weighting.

According to a further preferred embodiment of the invention, the first region of the multivariate optical element for modifying the polarization of the dispersed optical signal is configurable for generating configurable polarization modifications of the dispersed optical signal. In this way, the first multivariate optical element is implemented as a configurable polarization modulator. Such a configurable polarization modulator allows to modify the spectral ranges of the first and the second parts of the optical signal.

According to a further preferred embodiment of the invention, the transmission and/or reflectivity of the second region of the second multivariate optical element is configurable. In this way the second multivariate optical element can be universally adapted to a plurality of different spectral weighting functions. In particular, when both the first and the second multivariate optical elements are implemented as configurable elements, the optical analysis system can be universally adapted to arbitrary weighting functions. In this way the first multivariate optical element serves to separate position and negative parts of the weighting function and the second multivariate optical element serves to scale or to weight the amplitude and/or intensity of a received optical signal in a way that is specified by the weighting function.

Configuration of the first and/or the second MOE is particularly advantageous to adjust the optical analysis system to different principal components of the optical signal. In this way, not only a single amplitude of a single principal component of an optical signal can be obtained but moreover a whole variety of amplitudes of various principal components may allow to determine various concentrations of different substances of a sample.

According to a further preferred embodiment of the invention, the first and/or the second multivariate optical elements comprise at least one configurable transmissive or reflective liquid crystal cell. Depending on the implementation of the liquid crystal cell, the entire optical analysis system can be operated in a transmission. or reflection geometry. The liquid crystal cell provides an array of cell elements that can be separately controlled by applying an appropriate voltage. Preferably, the liquid crystal cell serves as a spatial polarization modulator, i.e. the single cell elements provide a modification of the polarization state of an incident optical signal. The magnitude of the polarization modification is governed by the amplitude of the voltage that is applied to each cell element.

Implementation of the first multivariate optical element on the basis of a liquid crystal cell can be effectively realized by making use of the liquid crystal cell in combination with a polarizing beam splitter. Assuming that the incident dispersed optical signal is linearly polarized, the liquid crystal cell may modify the polarization state of a particular spectral range of the dispersed optical signal by 90 degrees. Consequently, this particular spectral range will experience a separation from the optical signal upon propagation through a polarizing beam splitter.

Implementation of a transmissive or reflective liquid crystal cell into the second multivariate optical element can be effectively realized by arranging the liquid crystal cell between crossed polarizers. The configuration of crossed polarizers and the liquid crystal cell serves as a spatial amplitude modulator that is adapted to attenuate an optical signal thus imprinting a variety of grey values. Depending on the applied voltage the various cell elements provide different values of transmission. Combining such a spatial amplitude modulator with the dispersive element particular spectral ranges of the optical signal can be effectively weighted.

According to a further preferred embodiment of the invention, the first multivariate optical element comprises a dichroic element that is adapted to spatially separate the first and the second part of the optical signal. Instead of making use of a combination of a dispersive optical element and a spatial light modulator this embodiment provides a rather intuitive approach to spatially separate various spectral ranges or bands of an optical signal. The dichroic element which is preferably implemented as a dichroic mirror is not configurable and has to be designed for each. weighting function that specifies positive and negative parts of a principal component. Positive and negative parts of the principal component typically refer to the first and second parts of the optical signal. They are by no means restricted to a specific spectral interval. Moreover, each part of the optical signal may refer to various spectral intervals or spectral ranges of the optical signal and a respective combination thereof.

However, by implementing the first multivariate optical element as a dichroic element, the optical analysis system can be realized in a non complicated and low cost way. This is particularly advantageous, when the optical analysis system is dedicated to the spectral analysis of a particular substance that consists of a few compounds that have large spectral differences. In this way, the transmission and reflection properties of the dichroic element have to be adaptively designed to the spectrum of the substance and its corresponding weighting function.

According to a further preferred embodiment of the invention, the optical analysis system further comprises a polarization conversion element. Since for many embodiments of the invention it is particularly advantageous that the incident optical signal is linearly polarized, the polarization conversion element serves to convert an arbitrarily polarized optical signal into a linearly polarized optical signal. Preferably, the polarization conversion element is implemented by making use of a polarizing beam splitter and a retarding wave plate, preferably a half-wave plate. Arbitrarily polarized light can in principle be represented as a superposition of s- and p-polarized light. Ideally, the polarizing beam splitter separates s-polarized and p-polarized light that emerges at different angles from the polarization beam splitter. Consequently, the two evolving light beams are either s- or p-polarized. Making use of a half-wave plate in order to rotate the polarization direction of one of these beams, two light beams that have the same polarization direction can be effectively generated. Additionally, these light beams can be combined to a single light beam that is linearly polarized. In this way linearly polarized light can be effectively generated without applying a linear polarizer that absorbs an appreciable amount of intensity.

According to a further preferred embodiment of the invention, the optical analysis system further comprises a light source for providing light for illuminating a sample comprising a substance that has a concentration and thereby generates the principal component. The amplitude of the principal component relates to the; concentration of the substance.

In another aspect the invention provides a blood analysis system that comprises an optical analysis system as described above. Here, the sample illuminated by light comprises blood.

In still another aspect the invention provides a method of determining an amplitude of a principal component of an optical signal. The method comprises the steps of separating the optical signal into a first and a second part, weighting of the optical signal and detecting the weighted first and second parts of the optical signal.

Further, it is to be noted that any reference sign in the claims are not to be construed as limiting the scope of the present invention.

BRIEF DESCRIPTION OF THE DRAWINGS

In the following preferred embodiments of the invention will be described in detail by making reference to the drawings in which.

DESCRIPTION

Figure 1:
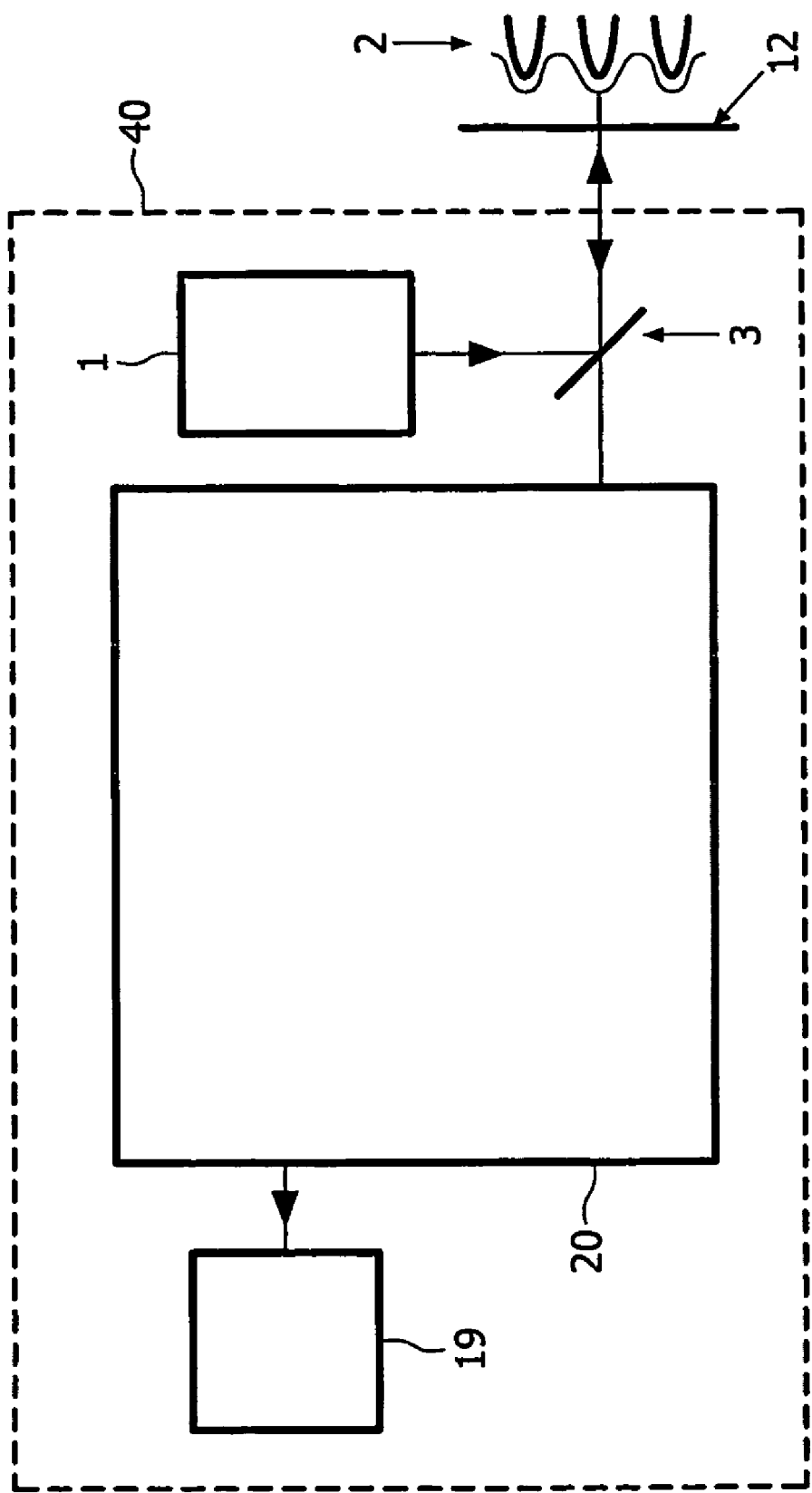
FIG. 1 is a schematic diagram of an embodiment of the blood analysis system.

In the embodiment shown in FIG. 1 the optical analysis system 20 for determining an amplitude of a principal component of an optical signal comprises a light source 1 for providing light for illuminating a sample 2 comprising a substance having a concentration and thereby generating the principal component. The amplitude of the principal component relates to the concentration of the substance. The light source 1 is a laser such as a gas laser, a dye laser and/or a solid state laser such as a semiconductor or diode laser.

The optical analysis system 20 is part of a blood analysis system 40. The blood analysis system further comprises a computational element 19 for determining the amplitude of the principal component, hence for determining the composition of the compound. The sample 2 comprises skin with blood vessels. The substance may be one or more of the following analytes: glucose, lactate, cholesterol, oxy-hemoglobin and/or desoxy-hemoglobin, glycohemoglobin (HbA1c), hematocrit, cholesterol (total, HDL, LDL), triglycerides, urea, albumin, creatinin, oxygenation, pH, bicarbonate and many others. The concentrations of these substances is to be determined in a non-invasive way using optical spectroscopy. To this end the light provided by the light source 1 is sent to a dichroic mirror 3 which reflects the light provided by the light source towards the blood vessels in the skin. The light may be focused on the blood vessel using an objective 12. The light may be focused in the blood vessel by using an imaging and analysis system as described in the international patent application WO 02/057759.

By interaction of the light provided by the light source 1 with the blood in the blood vessel an optical signal is generated due to Raman scattering and fluorescence. The optical signal thus generated may be collected by the objective 12 and sent to the dichroic mirror 3. The optical signal has a different wavelength than the light provided by the light source 1. The dichroic mirror is constructed such that it transmits at least a portion of the optical signal.

Figure 2A:
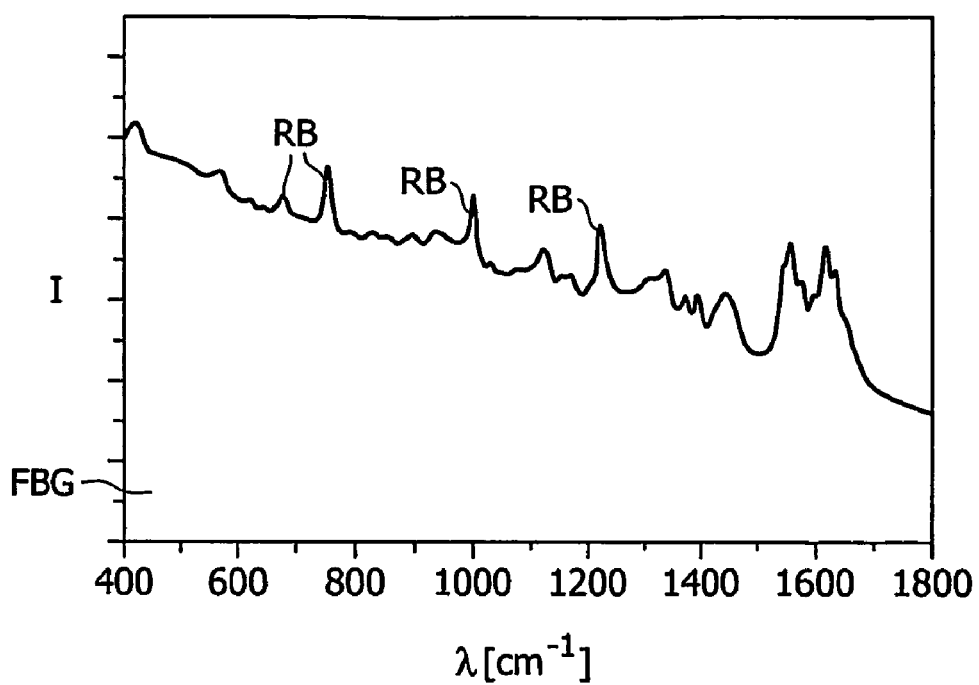
FIGS. 2a and 2b are spectra of the optical signal generated from blood in the skin and from a sample comprising one analyte in a solution.

A spectrum of the optical signal generated in this way is shown in FIG. 2A. The spectrum comprises a relatively broad fluorescence background (FBG) and relatively narrow Raman bands (RB). The x-axis of FIG. 2A denotes the wavelength shift with respect to the 785 nm of the excitation by light source 1 in wave numbers, the y-axis of FIG. 2A denotes the intensity in arbitrary units. The x-axis corresponds to zero intensity. The wavelength and the intensity of the Raman bands, i.e. the position and the height, is indicative for the type of analyte as is shown in the example of FIG. 2B for the analyte glucose which was dissolved in a concentration of in water.

Figure 2B:
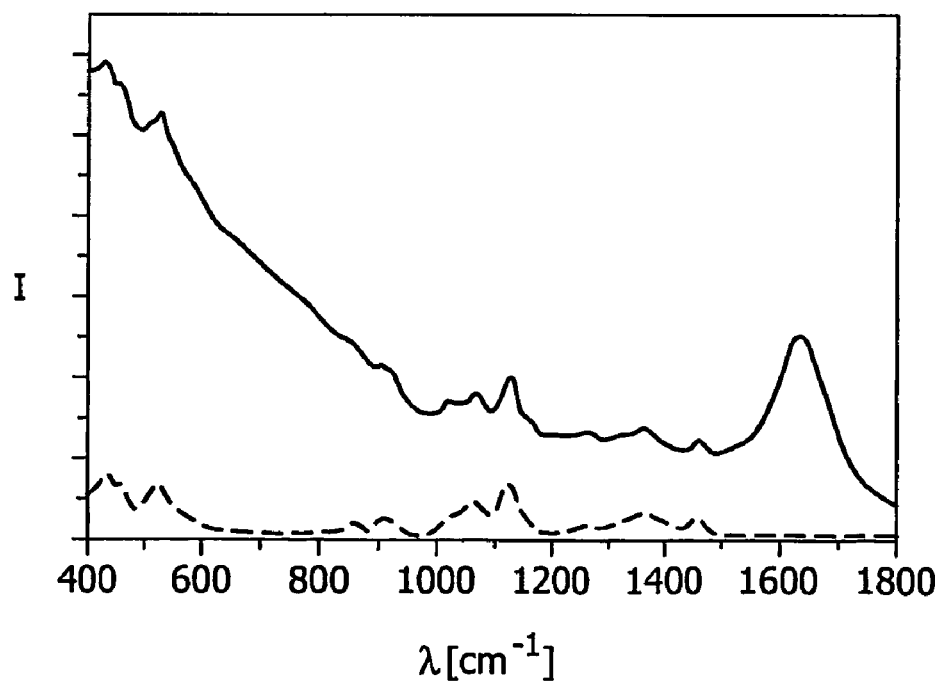
Figure 3:
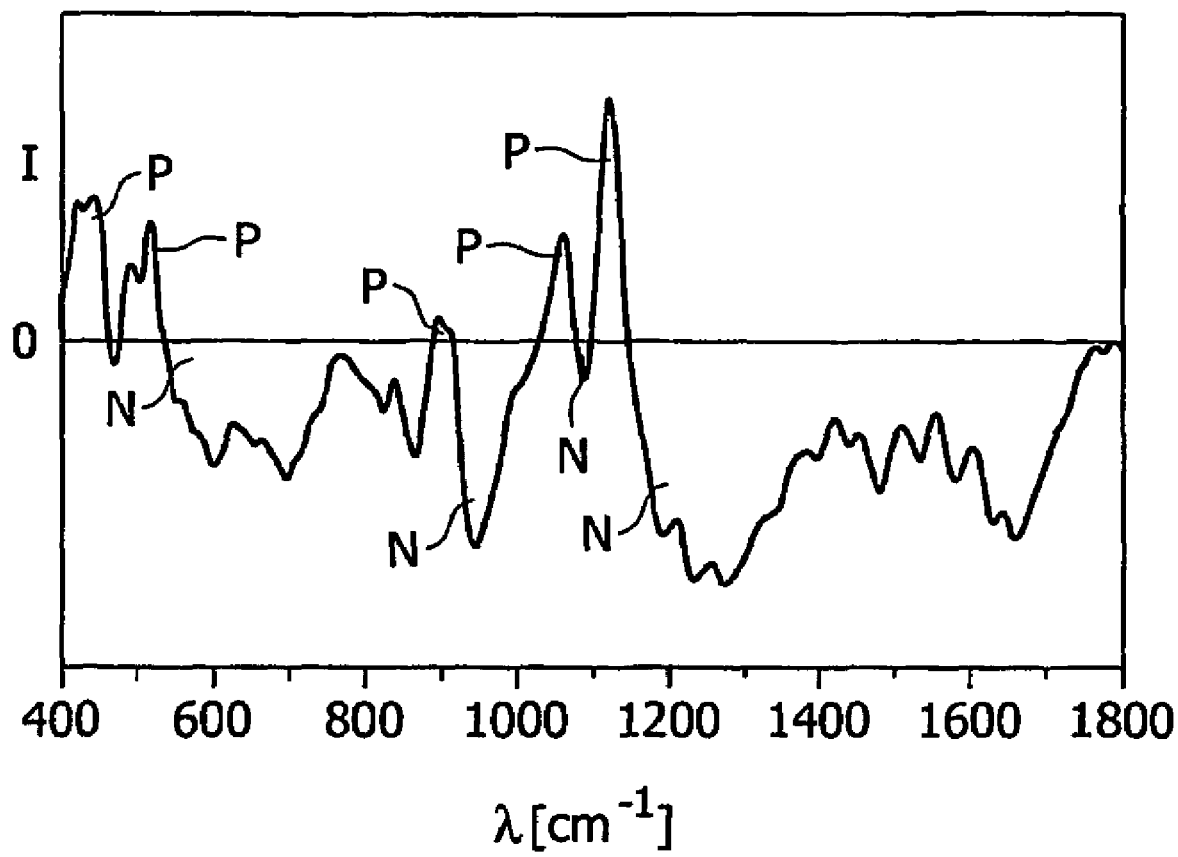
FIG. 3 is a spectral weighting function implemented in a MOE.

Because blood comprises many compounds each having a certain spectrum which may be as complex as that of FIG. 2B, the analysis of the spectrum of the optical signal is relatively complicated. The optical signal is sent to the optical analysis system 20 according to the invention where the optical signal is analyzed by a MOE which weights the optical signal by a weighting function shown e.g. schematically in FIG. 3. The weighting function of FIG. 3 is designed for glucose in blood. It comprises a positive part P and a negative part N. The positive part P and the negative part N each comprise in this example more than one spectral band.

Here and in the remainder of this application the distance between a focusing member and another optical element is defined as the distance along the optical axis between the main plane of the focusing member and the main plane of the other optical element.

A computational element 19 shown in FIG. 1 is arranged to calculate the difference between the positive and negative signal. This difference is proportional to the amplitude of the principal component of the optical signal. The amplitude of the principal component relates to the concentration of the substance, i.e. of the analyte. The relation between the amplitude and the concentration may be a linear dependence.

Figure 4:
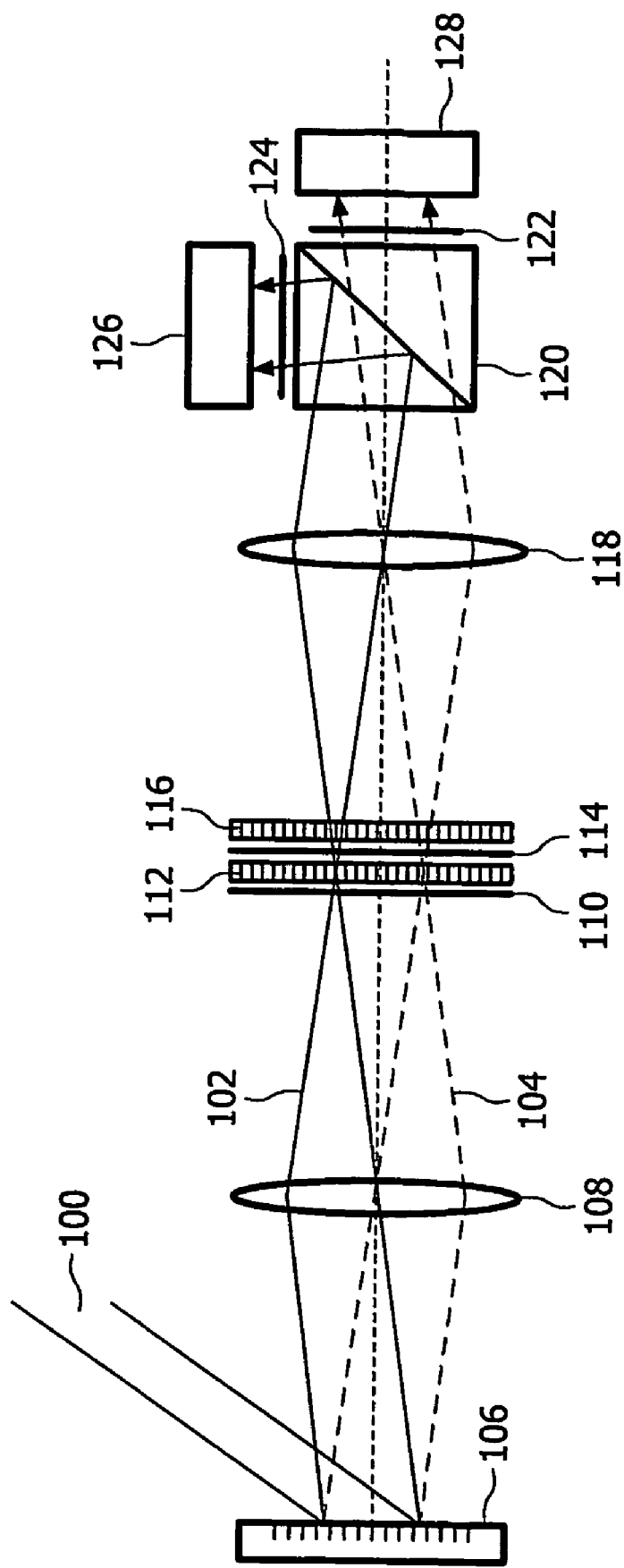
FIG. 4 is a schematic diagram of an embodiment of the optical analysis system.

FIG. 4 illustrates a schematic diagram of an embodiment of the optical analysis system. The optical analysis system comprises a dispersive element 106, lenses 108, 118, two liquid crystal cells 112, 116, four polarizers 110, 114, 122, 124, a polarizing beam splitter 120 and two separate detectors 126, 128. An optical signal 100 featuring a spectrum being indicative of the composition of a substance is incident on the dispersive optical element 106. The dispersive optical element 106 can be implemented as a grating, or any other dispersive optical element like e.g. a prism.

The dispersive optical element 106 provides spectral dispersion of the optical signal 100. As an example, two different spectral components 102 and 104 are depicted in FIG. 4. The two spectral components 102, 104 are reflected at the dispersive element 106 at different angles. For simplification only two representative rays of the spectral components 102, 104 are illustrated as a solid and dashed line, respectively. The two spectral components 102, 104 propagate through the lens 108 that provides focusing of the spectral components on the liquid crystal cell 112.

The liquid crystal cell 112 is sandwiched between two crossed polarizers 110, 114. Before the spectral components become incident on the first liquid crystal cell 112 they have to propagate through the polarizer 110. Consequently, the two spectral components 102, 104 are linearly polarized by means of the polarizer 110.

In this embodiment the liquid crystal cell 112 serves as a component of the second multivariate optical element for providing wavelength selective weighting of the optical signal 100. As can be seen the two spectral components 102, 104 are focused at different locations on the liquid crystal cell 112. At these locations respective liquid crystal cell elements provide a modification of the polarization state of the spectral components 102, 104 in order to separately attenuate or weight the two different spectral components 102, 104.

By means of the subsequent polarizer 114 which is rotated by 90 degrees with respect to the polarizer 110, the modification of the polarization state of the spectral components 102, 104 transforms into a respective intensity modification. This intensity modification typically corresponds to the weighting of the particular spectral components as given by the spectral weighting function. Hence the second multivariate optical element for wavelength selective weighting of the optical signal 100 can be effectively realized by means of the dispersive optical element 106, the liquid crystal cell 112 and the two crossed polarizers 110, 114.

After this wavelength selective weighting the two spectral components 102, 104 are incident on the liquid crystal cell 116. The liquid crystal cell 116 is a basic component of the first multivariate optical element for wavelength selective separation of the optical signal 100. The liquid crystal cell 116 is preferably adapted to selectively switch the polarization state of the spectral components 102, 104. For example, the spectral component 102 becomes s-polarized whereas the spectral component 104 becomes p-polarized. The two separate spectral components 102, 104 propagate through the lens 118 and become incident on the polarizing beam splitter 120. For example, the polarizing beam splitter 120 is adapted to reflect s-polarized light towards the detector 126 and to transmit p-polarized light towards the detector 128. In this way the spectral component 102 that became s-polarized by means of the liquid crystal cell 116 is entirely detected by the detector 126 and the spectral component 104 that became p-polarized by means of the liquid crystal cell 116 is entirely transmitted by the polarizing beam splitter and subsequently detected by the detector 128.

The additionally illustrated polarizers 124 and 122 are optional polarizers that serve to prevent crosstalk between the two spectral components and to compensate for imperfections of the polarizing beam splitter 120. Therefore, polarizer 124 is arranged to transmit s-polarized light whereas polarizer 122 is arranged to transmit p-polarized light. In this way, the first multivariate optical element for wavelength selective separation of the optical signal into a first part and a second part is effectively realized by means of the liquid crystal cell 116, the dispersive optical element 106 and the polarizing beam splitter 120.

FIG. 4 already illustrates a rather sophisticated embodiment of the present invention, where the first multivariate optical element and the second multivariate optical element are implemented in a combined way. This means that both multivariate optical elements comprise a plurality of optical components that in combination provide the functionality of the two multivariate optical elements. For example, the dispersive optical element 106 is a optical component used for both multivariate optical elements.

In particular due to the implementation of the first multivariate optical element by making use of a liquid crystal cell in combination with a polarizing beam splitter almost no light intensity is lost in order to separately detect the different spectral components of the optical signal 100. Referring to the weighting function illustrated in FIG. 3, the liquid crystal cell 116 serves to switch positive and negative parts of the received dispersive optical signal to either s-polarized or p-polarized polarization states. In this way each detector 126, 128 only detects p-polarized or s-polarized light that corresponds to positive or negative parts of the weighting function.

Similarly, the liquid crystal cell 112 in combination with the two crossed polarizers 110, 114 serves to weight the received dispersed optical signal according to the values given by the weighting function.

In the embodiment shown in FIG. 4 both multivariate optical elements are implemented as configurable multivariate optical elements. In this way the optical analysis system can be universally adapted to various weighting functions in order to determine the concentration of different substances in the sample. For each substance the two liquid crystal cells 112, 116 have to be configured in a way that corresponds to the respective weighting function.

Since the optical signal 100 is typically rather low in intensity, making use of the polarizer 110 may reduce the provided intensity. It would be therefore rather advantageous to replace the polarizer 110 by a polarization conversion element 150.

Figure 5:
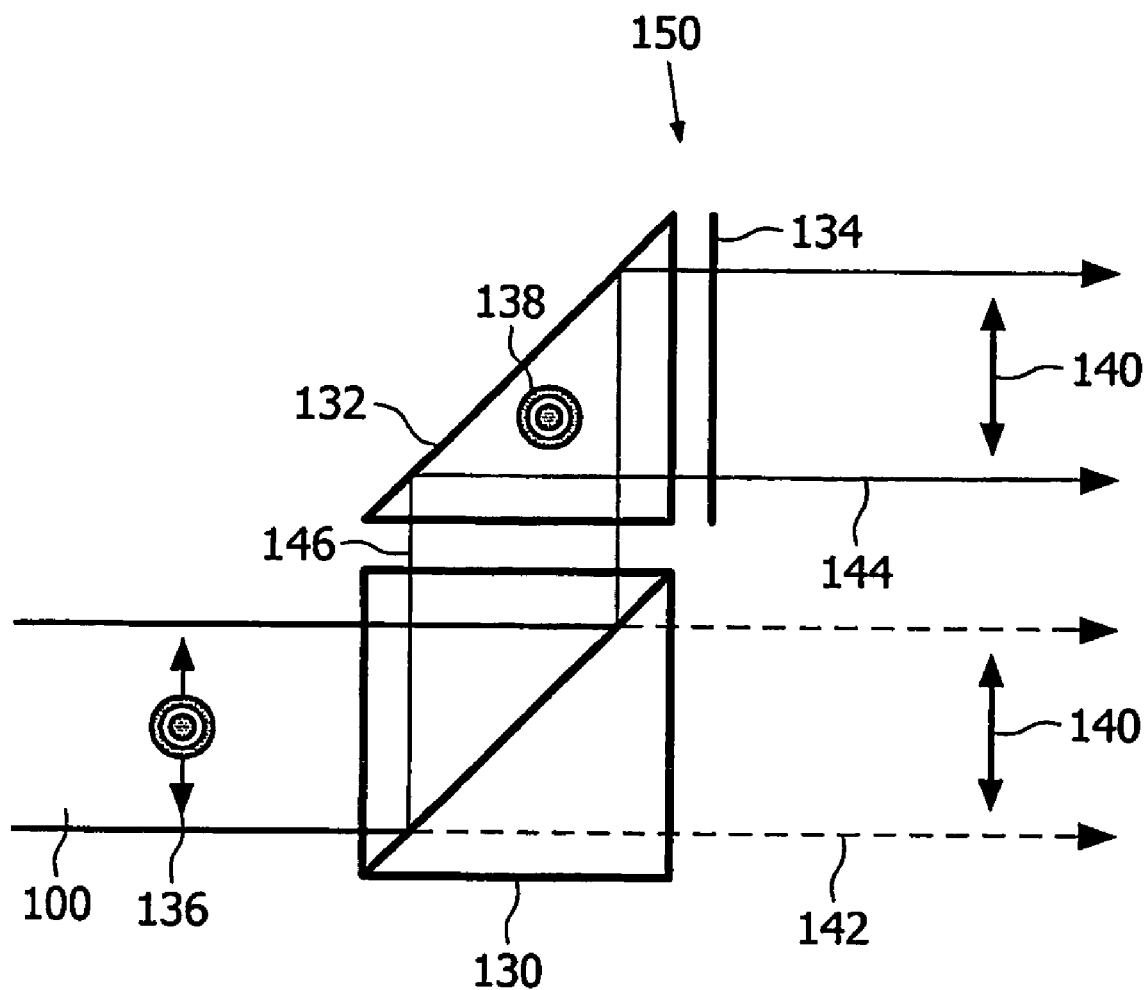
FIG. 5 is a schematic diagram of the polarization conversion element.

FIG. 5 is illustrative of such a polarization conversion element 150 that comprises a polarizing beam splitter 130, a prism 132 and a half-wave plate 134. Typically, the spectroscopic optical signal 100 that is generated by e.g. a Raman process has a mixed polarization state which is indicated by the symbol 136. However, a mixed polarization state can always be represented as a superposition of s- and p-polarizing states. Upon propagation of the optical signal 100 through the polarizing beam splitter 130, for example p-polarized light 142 is transmitted, whereas s-polarized light 146 is reflected.

The different mutual orthogonal polarization states of the s and p-polarized components 146, 142 is indicated by the symbols 138, 140 indicating the direction of polarization, respectively. The reflected s-polarized light 146 is reflected by the prism 132 and finally propagates through the half-wave plate 134. When appropriately arranged, the half-wave plate 134 exactly rotates the plane of polarization of the s-polarized light 146 by 90 degrees to become p-polarized light 144. In this way the polarization conversion element 150 effectively generates two separate light beams 142, 144 that have the same polarization direction. Additionally, the two generated light beams 142, 144 can be combined before they enter the optical analysis system as. optical signal 100. Making use of such a polarization conversion element 150, a polarizer 110 as depicted in FIG. 4 becomes obsolete. In this way attenuation of the optical signal is reduced to a minimum in order to increase the signal to noise ratio of the detected spectral components 102, 104.

Figure 6:
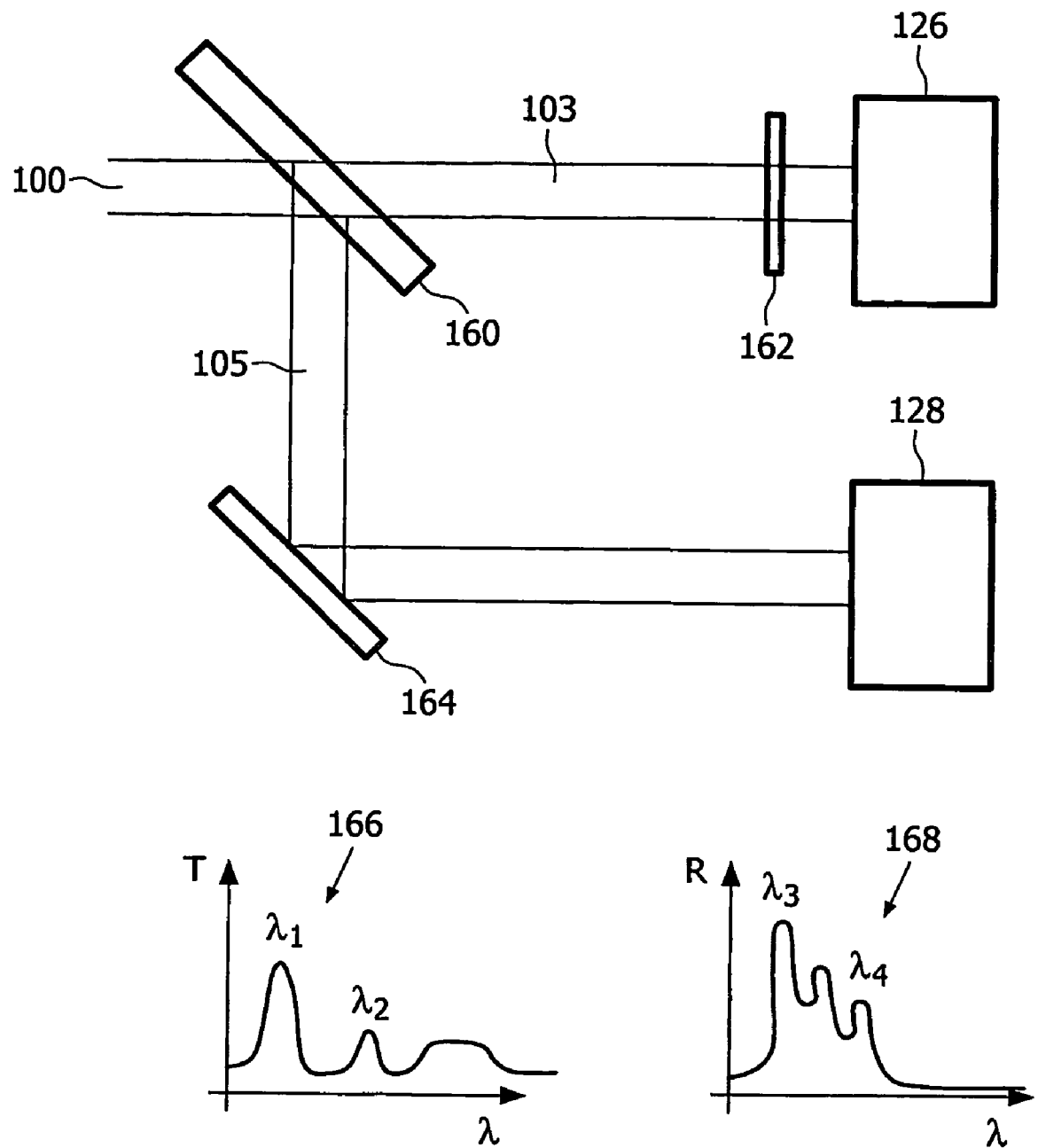
FIG. 6 is a schematic diagram of another embodiment of the invention.

FIG. 6 schematically illustrates another embodiment of the invention. Here, the first multivariate optical element is implemented as a dichroic mirror 160. The optical signal 100 is incident on the dichroic mirror 160 that serves as the first multivariate optical element. The dichroic mirror is particularly designed for transmission and reflection of spectral bands that correspond to positive and negative parts of the spectral weighting function shown e.g. schematically in FIG. 3. For example, the spectral component 103 corresponds to positive spectral bands and the reflected spectral component 105 corresponds to negative spectral band of the optical signal 100. In this example the positive part and the negative part 103, 105 correspond to more than just one spectral band. In this way the first multivariate optical element is exclusively implemented by means of the dichroic mirror 160. It effectively provides spatial separation of spectral bands of the optical signal 100 that correspond to positive and negative parts of the spectral weighting function. It is to be noted that in this way spatial separation of the positive and negative spectral bands can be performed without significant loss in intensity.

After separation into positive and negative spectral bands, the respective bands are separately detected by detectors 126 and 128. Before detection, each of the spectral components 103, 105 becomes subject to wavelength selective amplitude modulation. This wavelength selective amplitude modulation is typically performed by means of the second MOE that is separately implemented as a wavelength selective filter 162 and a wavelength selective mirror 164. The spectral component 103 propagates through the filter 162 that has a particular transmission property illustrated by the transmission diagram 166. In this way selective wavelengths $\lambda_1$ and $\lambda_2$ can be selectively attenuated while the remaining spectrum is effectively suppressed. In a similar manner the wavelength selective mirror 164 provides wavelength selective reflection of the spectral component 105. Light reflected at the mirror 164 is then detected by means of the detector 128. Similarly as the transmission diagram 166 of the wavelength selective filter 162, the wavelength selective mirror 164 provides a reflection diagram 168 for reflecting only particular wavelengths $\lambda_3$ and $\lambda_4$ of the spectral component 105.

In this embodiment the first MOE is implemented as a dichroic mirror and the two second MOEs providing effecting weighting of the spatially separated. spectral components 103 and 105 are implemented as wavelength selective optical transmission or reflection components 162, 164, respectively. In this way the inventive optical analysis system can be implemented with a limited amount of optical components that are dedicated to determine an amplitude of a distinct principal component. Hence the wavelength selective components 160, 162, 164 are particularly designed for a distinct application typically at the expense of not being configurable. In contrast to the embodiment shown in FIG. 4 the embodiment of FIG. 6 represents a rather uncomplicated and low cost approach for realizing the optical analysis system. Even though the approach illustrated in FIG. 6 makes use of wavelength selective transmission and/or reflection, relevant portions of the spectral band ($\lambda_1$, $\lambda_2$, $\lambda_3$, $\lambda_4$) are not necessarily attenuated or blocked. Preferably, only portions of the spectrum that are irrelevant for the determination of the amplitude of the principal component are effectively discarded.

Figure 7:
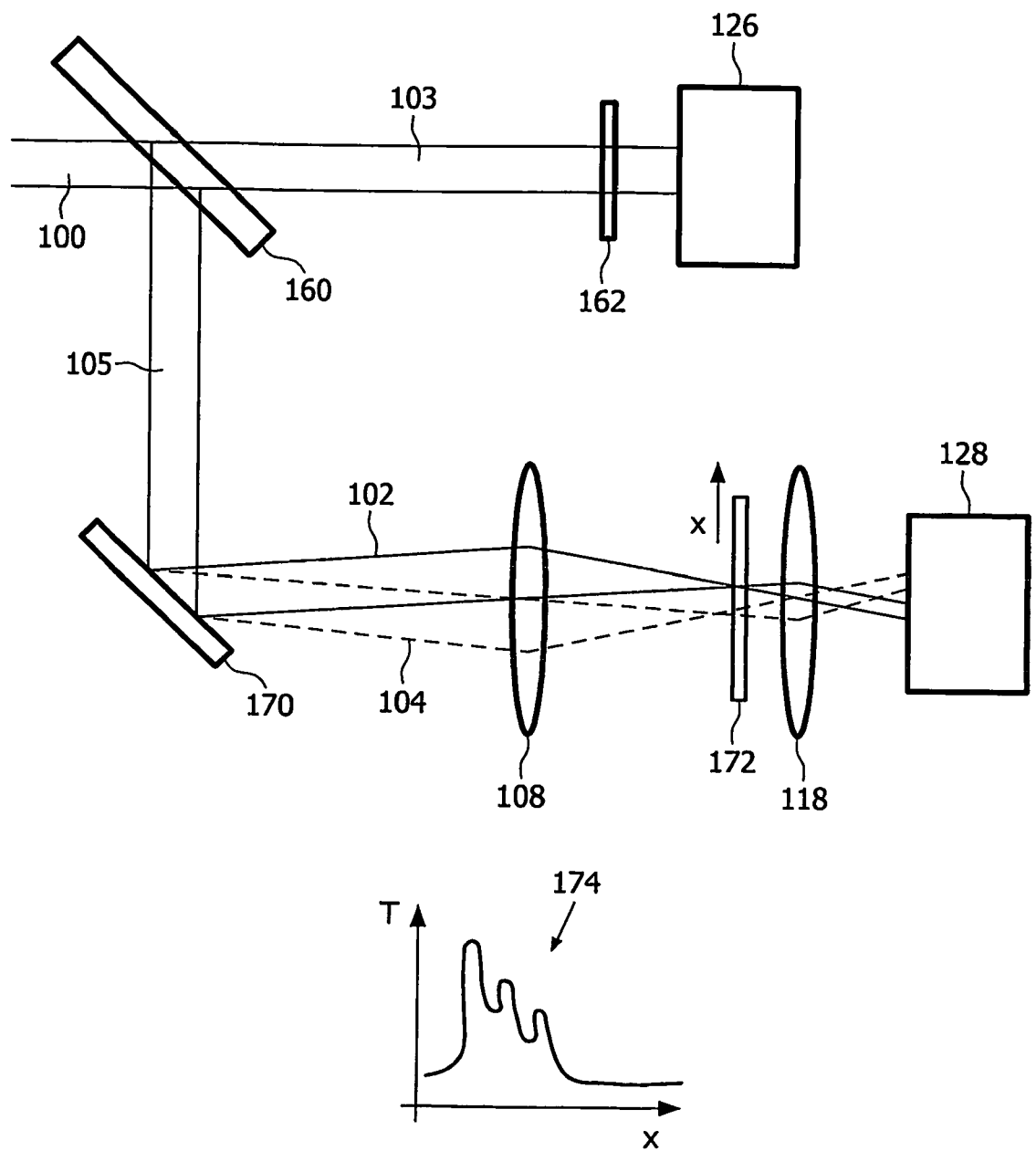
FIG. 7 is a schematic diagram of an alternative embodiment of the optical analysis system.

FIG. 7 shows an alternative embodiment of FIG. 6, where the second MOE 164 of FIG. 6 is replaced by an arrangement comprising a grating 170, a filter 172 and two focusing elements 108, 118. Here, the first MOE is similarly implemented as shown in FIG. 6 by means of the dichroic mirror 160. Also here, spectral bands 103, 105 corresponding to positive and negative parts of the spectral weighting function are separately detected by means of the detectors 126 and 128, respectively. Instead of making use of a wavelength selective mirror 164 as shown in FIG. 6, the embodiment of FIG. 7 makes use of the grating 170 for spatial separation of various spectral components 102, 104 of the spectral component 105. Similarly as shown in FIG. 4 the two spectral components 102, 104 are only representative of a plurality of spectral components of the negative part of the spectrum. They are depicted as solid and dashed. lines. By means of the lens 108, the two spectral components 102, 104 are incident at different positions of the filter 172.

The filter 172 provides a particular spatial transmission diagram 174. The spatial direction x is indicated in the vertical direction near the filter 172. Since various spectral components 102, 104 are incident at different positions x at the filter 172, these spectral components become subject to selective attenuation as given by the transmission diagram 174 of the filter 172. In this way the second MOE for realizing a wavelength selective weighting of the optical signals is realized by means of a grating 170 and a filter 172 that has a spatially varying transmission curve. The filter 172 can be implemented as a particularly designed transmission mask. Alternatively, the filter 172 can be realized by making use of a liquid crystal cell that is sandwiched between crossed polarizers. In the latter rather sophisticated embodiment, the filter 172 might be configurable.

Figure 8:
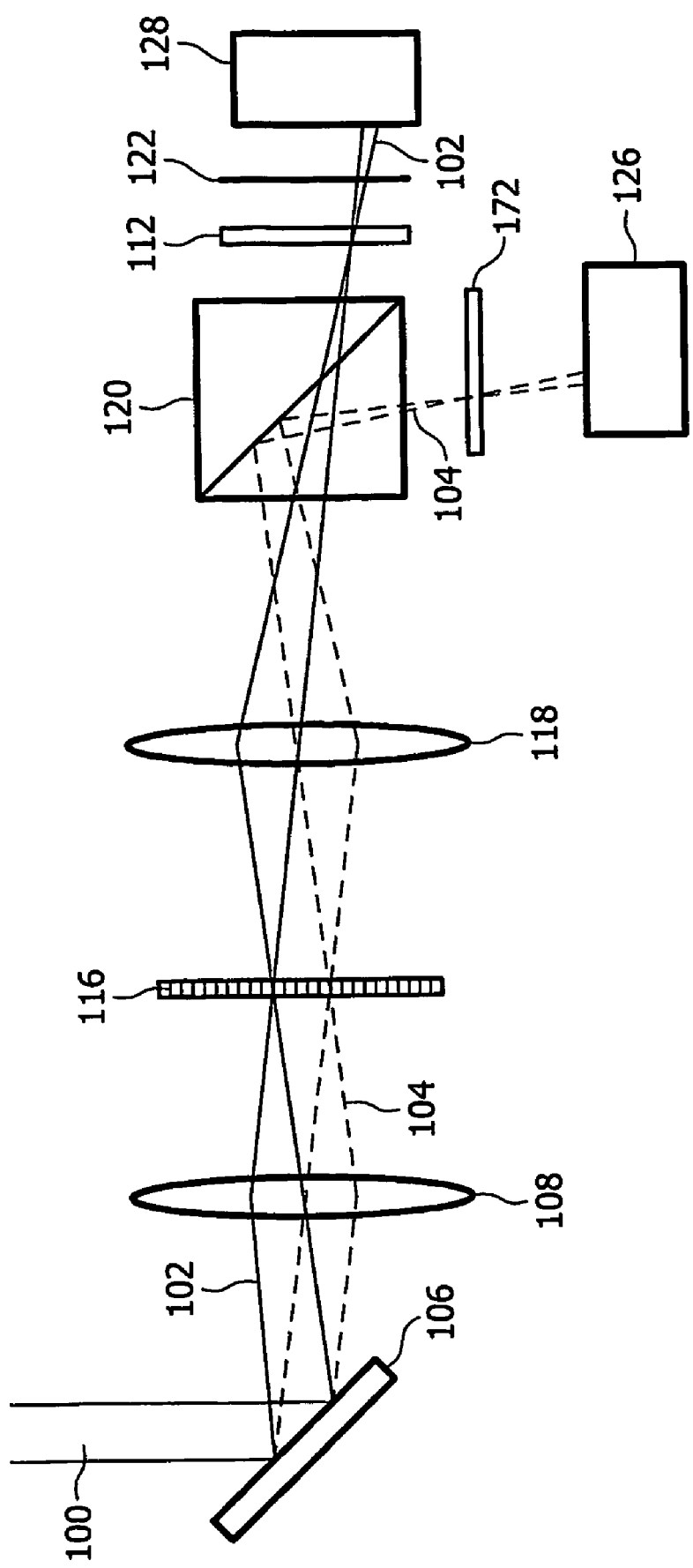
FIG. 8 is a schematic diagram of another embodiment of the optical analysis system.

FIG. 8 is illustrative of a schematic diagram of an alternative embodiment of the invention. The embodiment of FIG. 8 has a certain similarity with the embodiment illustrated in FIG. 4, except that the effective order of the first and the second MOEs is interchanged. In the embodiment of FIG. 8, the optical signal 100 is incident on the dispersive optical element 106 that provides reflection of various spectral components 102, 104 of the optical signal 100 at various reflection angles. After propagation through the lens 108 the two spectral components 102, 104 are incident on a liquid crystal cell 116. Here, it is to be assumed that the spectral components 102, 104 are linearly polarized by e.g. making use of the polarization conversion element 150 depicted in FIG. 5. Otherwise a polarizer 110 may be inserted prior to the liquid crystal cell 116.

Preferably, the liquid crystal cell 116 is configurable in order to selectively modify the polarization state of the two spectral components 102, 104. For example, spectral component 102 becomes p-polarized and spectral component 104 becomes s-polarized. The two mutually orthogonal polarized spectral components 102, 104 propagate through the lens 118 and become incident on the polarizing beam splitter 120. The polarizing beam splitter 120 provides transmission of the p-polarized spectral component 102 and reflection of the s-polarized spectral component 104. The p-polarized and s-polarized spectral components are then separately detected by means of the detectors 128, 126, respectively. In this way the first MOE is implemented by means of a grating 106, the liquid crystal cell 116 and the polarizing beam splitter 120. The p- and s-polarized spectral components 102, 104 correspond to positive and negative spectral bands of the weighting function as illustrated e.g. in FIG. 3.

After spatially separating the spectral components 102, 104 corresponding to positive and negative parts of the spectral weighting function, the wavelength selective weighting has to be performed by means of a second MOE for each of the two components 102, 104. Principally, implementation of the second MOE can be realized analogously to any of the embodiments described with reference to FIGS. 4, 6, 7. Consequently, the second MOE can be realized as a wavelength selective filter 162, a wavelength selective mirror 164, or by making use of optical elements that provides a spatial transmission diagram similar as the spatial filter 172 or the spatial light modulator comprising a liquid crystal cell 112 and a pair of cross polarizers 110, 114 as shown in FIG. 4.

In FIG. 8 the second MOE for wavelength selective weighting of the spectral component 102 is implemented as a liquid crystal cell 112 and a subsequent polarizer 122. The second MOE for wavelength selective weighting of the spectral component 104 is implemented as a filter 172 that provides a transmission diagram 174 as depicted in FIG. 7. In this way both spectral components 102, 104 corresponding to positive and negative parts of the weighting function are separately weighted by means of two separate second MOEs. Hence, the two second MOEs of the embodiment of FIG. 8 are implemented as spatial light modulators in combination with a dispersive optical element 106.

Figure 9A:
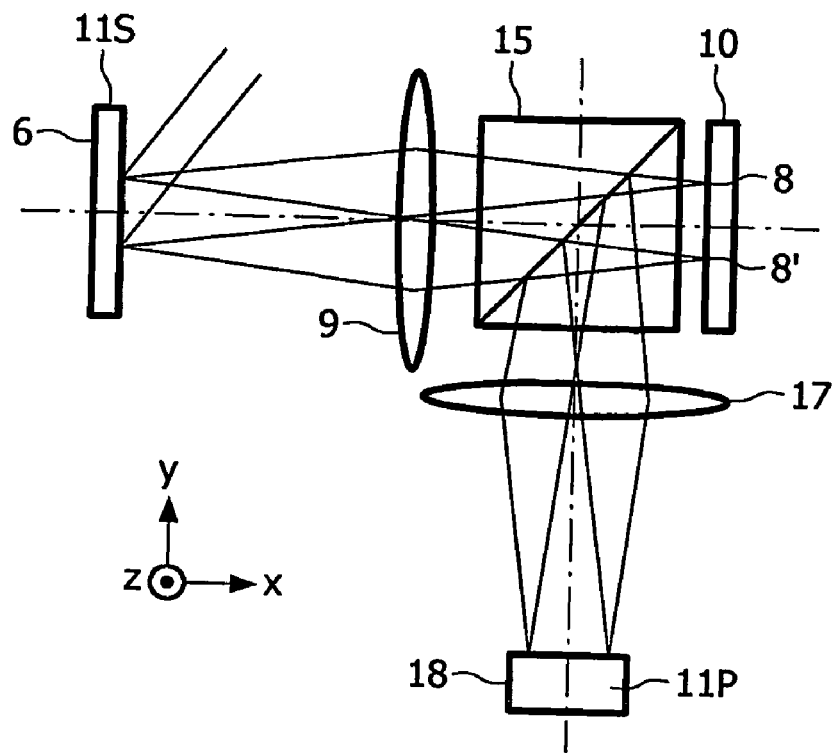
FIGS. 9a, 9b and 9c are schematic diagrams of yet. another embodiment of the optical analysis system in the x-y plane, the y-z plane and the x-z plane, respectively.
Figure 9B:
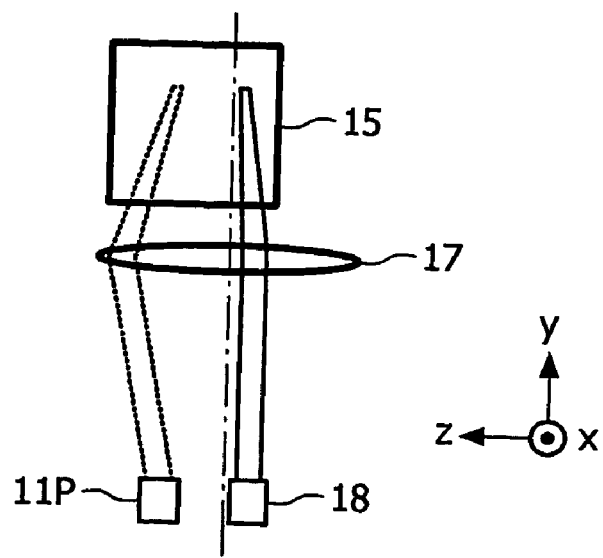
Figure 9C:
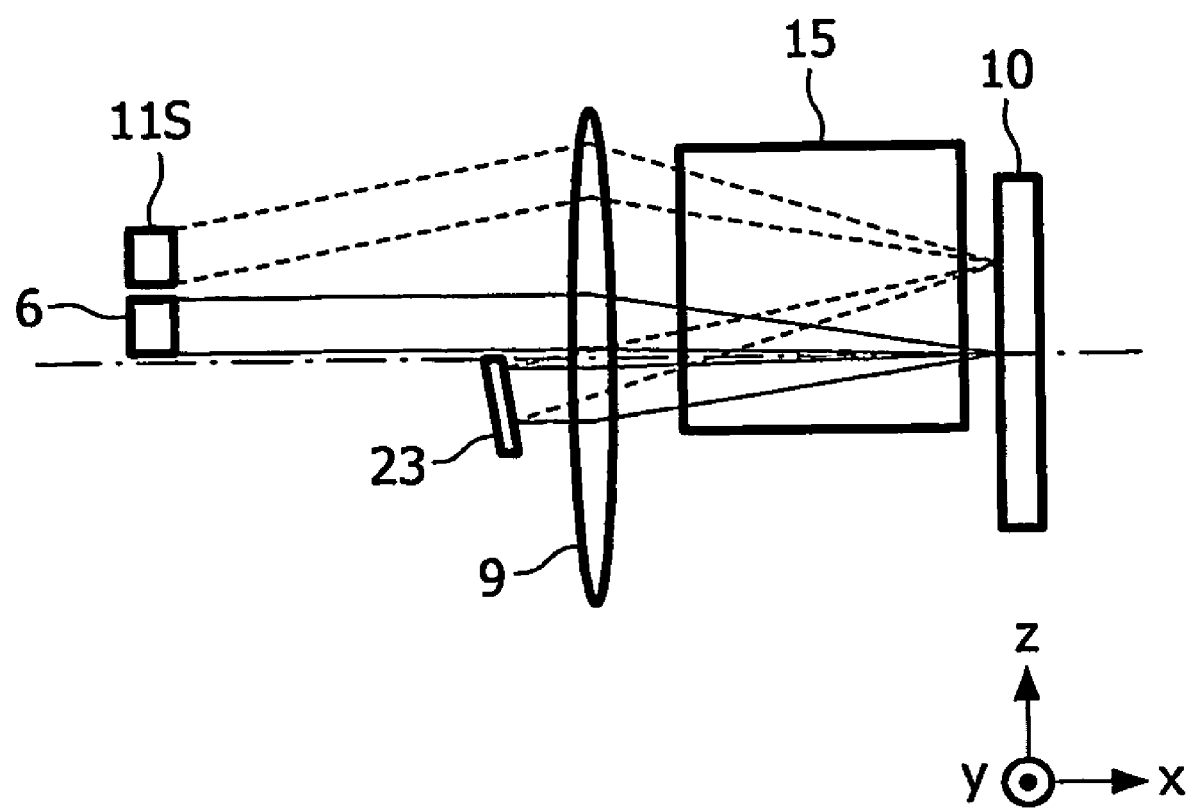

In another embodiment shown in FIGS. 9A, 9B and 9C the functionality of the first and the second MOE is merged in a single MOE 10. The MOE 10 comprises an array of LC cells. Additionally, the incoming optical signal is not split into two beams for the positive and negative part prior to the dispersive element 6 in this embodiment. The LC cell used in this embodiment is similar to that described above but does not contain a polarizer. The result is that substantially all, except for unwanted loss in the layer of the LC molecules, incident light is reflected, however the polarization direction of the light may be changed due to the anisotropic index of refraction which may be adjusted by application of a voltage across the LC cell. In FIG. 9A only one incoming beam with only p-polarized light is shown. The incoming light may be unpolarized or partially polarized having e.g. linear or circular polarization. In these cases the incoming beam may be decomposed into two beams having p-polarization and s-polarization analogously to the embodiment described above. For reasons of clarity only a single beam is drawn in FIGS. 9A, 9B and 9C.

In FIG. 9a the incoming light is the part of the optical signal having p-polarization, which is parallel to the z-axis direction. The incoming light is incident on a dispersive element 6 where the optical signal is spectrally dispersed, i.e. the different spectral portions are dispersed over different angles. The dispersed optical signal is at least partly collected by a focusing member 9, which is a lens, and focused on a MOE which is an array of reflective LC cells. The distances from the grating to the lens and from the lens to the LC cell are equal and correspond to the focal distance of the lens (telecentric design). The result is that converging pencils of light propagating towards the MOE 10 are normal incident on the MOE 10 in the x-z plane, for all spectral portions of the optical signal. Different y-positions 8, 8' on the MOE 10 correspond to different spectral portions of the optical signal.

Between the focusing member 9 and the MOE 10 a polarizing beam splitter (PBS) 15 is positioned. The incoming, e.g. p-polarized, light is transmitted by PBS 15. The array of LC cells contains no polarization filter and, therefore, reflects substantially all the light incident thereon. The polarization direction of the light is changed by an amount depending on the voltages across the LC cells. The amount of polarization rotation is determined by the absolute value of the spectral weighting function in the respective spectral range. The light reflected from the LC cell is directed to the PBS 15. The s-component of the light incident on the PBS 15 is reflected by the PBS 15 and focused by a further focusing member 17 on a beam dump 18. The p-component of the light incident on the PBS 15 is transmitted by PBS 15 and incident on a folding mirror 23. In this way, by spatially varying the polarization of the dispersed optical signal and selectively directing non-s-polarized components towards the beam dump 18, a wavelength selective weighting of the optical signal is effectively implemented. Hence, by means of the first reflection at the MOE 10 and the subsequent polarization-sensitive spatial separation, a wavelength selective gray scaling of the transmitted p-polarized components effectively occurs. Therefore, the second MOE is effectively implemented by the first reflection at MOE 10.

The distance from folding mirror 23 to the lens is not equal to the focal length of the lens. The light reflected by folding mirror 23 is repeatedly focused by the focusing member 9 on the MOE 10. Because the folding mirror 23 is at a slight angle with respect to the direction of the incident light, the light reflected by the folding mirror 23 reaches the MOE 10 at a different z-position. Also the y-position of the light on the LC-cell 10 is reflected with respect to the optical axis compared to the y-position of the first reflection. At the different z-position the polarization of the incident dispersed optical signals is repeatedly subject to modification. Preferably, the incident spectral components become either s- or p-polarized as specified by the negative and positive parts of the weighting function or regression vector.

For light with a wavelength corresponding to positive values of the regression vector the polarization is not changed by the LC cell. This s-polarized light is transmitted for the fourth time by the PBS and focused by lens 9 on detector 11S. For light with a wavelength corresponding to negative values of the regression vector the polarization is rotated by 90 degrees by the LC cell. This s-polarized light is reflected by the PBS and focused by lens 17 on detector 11P. In this way, the second reflection at the MOE 10 provides separation of the optical signal into positive and negative parts and therefore represents the functionality of the first MOE.

In this embodiment the LC cell does not contain a polarizer. Therefore, all light is reflected and only the polarization direction of the light may be changed.

The incident light is not on the optical axis of the focusing member 9, therefore the incoming and returned light do not overlap and it is possible to use the folding mirror 23. Preferably the incoming light incident on the focusing member is of off-axis from the optical axis of the focusing member 9 and substantially perpendicular to the dispersion direction of the dispersive element 6 to allow for a relatively small lens diameter.

The distance from dispersive element 6 to the focusing member 9 and the distance from the focusing member 9 to the MOE 10 may be both equal to the focal length of the focusing member 9 (telecentric design). The result is that the converging pencils of light are normal incident on the MOE 10 in the x-z plane, for all spectral components.

The distance from the focusing member 9 to the detector 11S may be equal to the focal length of the focusing member 9. In this case the detector 11S may have a relatively small area.

The distance from the MOE 10 to the focusing member 17 and the distance the focusing member 17 to beam dump 18 and/or to the detector 11P may be each equal to the focal length of the focusing member 9 (telecentric design).

The distance from folding mirror 23 to the main plane of the focusing member 9 may be different from the focal length of focusing member 9 (non-telecentric design). In this way the detector 11S may have a different position than the dispersive element 6.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

LIST OF REFERENCE NUMERALS 1 light source
2 sample
3 dichroic mirror
6 dispersive optical element
9 focusing member
8 position on MOE
8' position on MOE
10 MOE
11S detector
11P detector
12 objective
15 Polarizing beam splitter
17 focusing member
18 beamdump
19 computational element
20 optical analysis system
23 folding mirror
40 blood analysis system
100 optical signal
102 spectral component
103 spectral component
104 spectral component
105 spectral component
106 dispersive optical element
108 lens
110 polarizer
112 liquid crystal cell
114 polarizer
116 liquid crystal cell
118 lens
120 polarizing beam splitter
122 polarizer
124 polarizer
126 detector
128 detector
130 polarizing beam splitter
132 prism
134 polarizer
136 polarization direction
138 polarization direction
140 polarization direction
142 p-polarized light
144 p-polarized light
146 s-polarized light
150 polarization conversion element
160 dichroic mirror
162 filter
164 mirror
166 transmission diagram
168 reflection diagram
170 dispersive optical element
172 filter
174 transmission diagram

The invention claimed is:

1. An optical analysis system for determining an amplitude of a principal component of an optical signal, the optical analysis system comprising:
   a first multivariate optical element for wavelength selective separation of the optical signal into a first part and a second part,
   a second multivariate optical element for wavelength selective weighting of the optical signal on the basis of a spectral weighting function,
   a first and a second detector for detecting the weighted first and second parts of the optical signal.

2. The optical analysis system according to claim 1, further comprising a dispersive optical element to spectrally disperse the optical signal, the first and the second multivariate optical elements arranged to receive the dispersed optical signal.

3. The optical analysis system according to claim 2, wherein the first multivariate optical element comprises a first region for receiving a spectral portion of the dispersed optical signal, the first region modifying the polarization of the dispersed optical signal.

4. The optical analysis system according to claim 3, wherein the first region of the multivariate optical element for modifying the polarization of the dispersed optical signal is configurable for generating configurable polarization modifications of the dispersed optical signal.

5. The optical analysis system according to claim 3, wherein the second multivariate optical element comprises a second region for receiving a spectral portion of the dispersed optical signal, the second region having a transmission or reflectivity relating to the spectral weighting function.

6. The optical analysis system according to claim 2, wherein the second multivariate optical element comprises a second region for receiving a spectral portion of the dispersed optical signal, the second region having a transmission or reflectivity relating to the spectral weighting function.

7. The optical analysis system according to claim 6, wherein the transmission and/or reflectivity of the second region of the second multivariate optical element is configurable.

8. The optical analysis system according to claim 1, wherein at least one of the first multivariate optical element and the second multivariate optical elements comprises at least one configurable transmissive or reflective liquid crystal cell.

9. The optical analysis system according to claim 1, wherein the first multivariate optical element comprises a dichroic element being adapted to spatially separate the first and the second part of the optical signal.

10. The optical analysis system according to claim 1, further comprising a polarization conversion element.

11. An optical analysis system according to claim 1, further comprising a light source for providing light for illuminating a sample comprising a substance having a concentration and thereby generating the principal component, the amplitude of the principal component relating to the concentration of the substance.

12. A method of determining an amplitude of a principal component of an optical signal, the method comprising the steps of:
separating the optical signal into a first part and into a second part by means of a wavelength selective multivariate optical element,
weighting of the optical signal on the basis of a spectral weighting function by means of a second multivariate optical element,
detecting the weighted first and second parts of the optical signal.

13. A blood analysis system comprising:
a first multivariate optical element for wavelength selective separation of an optical signal into a first part and a second part,
a second multivariate optical element for wavelength selective weighting of the optical signal on the basis of a spectral weighting function,
a first and a second detector for detecting the weighted first and second parts of the optical signal.

14. The blood analysis system of claim 13 further comprising a light source that is directed towards on sample, wherein the light source striking the sample creates the optical signal.

15. The blood analysis system according to claim 13, further comprising a dispersive optical element to spectrally disperse the optical signal; and wherein the first multivariate optical element comprises a first region for receiving a spectral portion of the dispersed optical signal, the first region modifying the polarization of the dispersed optical signal.

16. The optical analysis system according to claim 15, wherein the second multivariate optical element comprises a second region for receiving a spectral portion of the dispersed optical signal, the second region having a transmission or reflectivity relating to the spectral weighting function.

17. An optical analysis system for determining an amplitude of a principal component of an optical signal, the optical analysis system comprising:
a dispersive optical element which spectrally disperses the optical signal into a first spectral component and a second spectral component;
a first multivariate optical element which wavelength weights the first spectral component and the second spectral component on the basis of a spectral weighting function;
a second multivariate optical element which switches a polarization state of the weighted first spectral component and the weighted second spectral component of the optical signal; and
a first detector and a second detector which detect the weighted and polarized first and second spectral components of the optical signal.

* * * * *